United States Patent
Sharrock et al.

(10) Patent No.: US 7,239,394 B2
(45) Date of Patent: Jul. 3, 2007

(54) EARLY DETERMINATION OF ASSAY RESULTS

(75) Inventors: Stephen Paul Sharrock, Bedford (GB); Andrew Peter Phelan, Bedford (GB)

(73) Assignee: Inverness Medical Switzerland GmbH, Zug (CH)

( * ) Notice: Subject to any disclaimer, the term of this patent is extended or adjusted under 35 U.S.C. 154(b) by 434 days.

(21) Appl. No.: 10/741,416

(22) Filed: Dec. 19, 2003

(65) Prior Publication Data

US 2005/0037510 A1    Feb. 17, 2005

Related U.S. Application Data

(60) Provisional application No. 60/508,001, filed on Oct. 2, 2003.

(30) Foreign Application Priority Data

Jun. 4, 2003   (GB) ................ 0312815.4

(51) Int. Cl.
*G01N 21/00* (2006.01)
(52) U.S. Cl. .................................... 356/436
(58) Field of Classification Search ............. 356/436, 356/39; 204/403.01, 403.03
See application file for complete search history.

(56) References Cited

U.S. PATENT DOCUMENTS

| | | | |
|---|---|---|---|
| 4,399,362 A * | 8/1983 | Cormier et al. ............. 422/82 |
| 4,420,566 A | 12/1983 | Jessop et al. | |
| 4,523,853 A | 6/1985 | Rosenbladt et al. | |
| 4,676,653 A | 6/1987 | Strohmeier et al. | |
| 4,995,402 A | 2/1991 | Smith et al. | |
| 5,049,487 A | 9/1991 | Phillips et al. | |
| 5,114,350 A * | 5/1992 | Hewett ................. 422/82.05 |
| 5,304,468 A | 4/1994 | Phillips et al. | |
| 5,344,754 A | 9/1994 | Zweig | |

(Continued)

FOREIGN PATENT DOCUMENTS

DE    196 28 562    1/1998

(Continued)

OTHER PUBLICATIONS

Search Report dated Dec. 1, 2003 for GB 0312815.4.

(Continued)

*Primary Examiner*—Gregory J. Toatley, Jr.
*Assistant Examiner*—Kara Geisel
(74) *Attorney, Agent, or Firm*—Scott E. Kamholz; Foley Hoag LLP

(57) ABSTRACT

A device for determining the result of an assay may include a computation circuit, responsive to a signal representing the amount of an analyte or the rate of accumulation of an analyte, to: compare the signal to a first threshold; compare the signal to a second threshold, the second threshold being less than the first threshold; generate an output signal if the signal exceeds the first threshold or the signal is less than the second threshold, the output signal indicative of a first result if the signal exceeds the first threshold, or, alternatively, the output signal indicative of a second result if the signal is less than the second threshold; and terminate the assay if the signal exceeds the first threshold or the signal is less than the second threshold.

27 Claims, 5 Drawing Sheets

U.S. PATENT DOCUMENTS

| | | | |
|---|---|---|---|
| 5,504,013 A | 4/1996 | Senior | |
| 5,580,794 A | 12/1996 | Allen | |
| 5,679,584 A * | 10/1997 | Mileaf et al. | 422/68.1 |
| 5,786,220 A | 7/1998 | Pronovost et al. | |
| 5,837,546 A | 11/1998 | Allen et al. | |
| 5,885,839 A | 3/1999 | Lingane et al. | |
| 5,889,585 A | 3/1999 | Markart et al. | |
| 5,968,835 A | 10/1999 | Aoki et al. | |
| 5,968,839 A | 10/1999 | Blatt et al. | |
| 6,055,060 A | 4/2000 | Bolduan et al. | |
| 6,156,271 A | 12/2000 | May | |
| 6,194,222 B1 | 2/2001 | Buechler et al. | |
| 6,235,241 B1 | 5/2001 | Catt et al. | |
| 6,399,398 B1 | 6/2002 | Cunningham et al. | |
| 6,448,067 B1 | 9/2002 | Tajnafoi et al. | |
| 6,707,554 B1 | 3/2004 | Miltner et al. | |
| 6,825,918 B2 | 11/2004 | Eisenmann et al. | |
| 6,951,631 B1 | 10/2005 | Catt et al. | |
| 7,018,847 B2 | 3/2006 | Mendel-Hartvig et al. | |
| 2002/0192833 A1 | 12/2002 | Pan et al. | |
| 2003/0180815 A1 | 9/2003 | Rawson et al. | |
| 2004/0152208 A1 | 8/2004 | Hutchinson | |
| 2004/0152209 A1 | 8/2004 | Zin et al. | |

FOREIGN PATENT DOCUMENTS

| | | |
|---|---|---|
| EP | 0 362 809 | 4/1990 |
| EP | 0 291 194 B1 | 2/1994 |
| EP | 0 653 625 | 11/1994 |
| EP | 0 728 309 B1 | 8/1997 |
| EP | 0 819 943 A2 | 1/1998 |
| EP | 0 826 777 | 3/1998 |
| EP | 0 833 145 | 4/1998 |
| EP | 0 782 707 B1 | 11/1998 |
| EP | 1046122 | 10/2000 |
| EP | 0 291 194 B2 | 7/2003 |
| EP | 0 291 194 B8 | 10/2003 |
| GB | 2365526 | 7/2000 |
| WO | WO94/04925 | 3/1994 |
| WO | WO99/35602 | 7/1999 |
| WO | WO00/19185 | 4/2000 |
| WO | WO2004/070353 | 8/2004 |

OTHER PUBLICATIONS

Search Report dated Jul. 3, 2006 for FR 0406067.

European Search Report dated Jul. 3, 2006 for EP 04 25 3076.

* cited by examiner

EARLY DETERMINATION OF ASSAY RESULTS

CROSS-REFERENCE TO RELATED APPLICATION

This application claims the benefit of U.S. Provisional Patent Application Ser. No. 60/508,001, filed Oct. 2, 2003, the entire contents of which are hereby incorporated herein by this reference.

FIELD

The disclosed subject matter relates to assay reading devices for the measurement of analytes. In particular it relates to electronic readers for use with assay test-strips which use optical methods of measurement.

BACKGROUND

Analytical devices suitable for home testing of analytes are now widely commercially available. One lateral flow immunoassay device suitable for this purpose for the measurement of the pregnancy hormone human chorionic gonadotropin (hCG) is sold by Unipath under the brand-name CLEARBLUE® and is disclosed in EP291194.

In particular EP291194 discloses an immunoassay device comprising a porous carrier containing a particulate labelled specific binding reagent for an analyte, which reagent is freely mobile when in the moist state; and an unlabelled specific binding reagent for the same analyte, which reagent is immobilised in a detection zone or test zone downstream from the unlabelled specific binding reagent. Liquid sample suspected of containing analyte is applied to the porous carrier whereupon it interacts with the particulate labelled binding to form an analyte-binding partner complex. The particulate label is coloured and is typically gold or a dyed polymer, for example latex or polyurethane. The complex thereafter migrates into a detection zone whereupon it forms a further complex with the immobilised unlabelled specific binding reagent enabling the extent of analyte present to be detected or observed. Due to the nature of the binding reactions taking place it is necessary to wait for a particular period of time to elapse after the test has commenced in order to read the result. This is particularly important for a visual semi-quantitative type of test whereby the result develops over time as the fluid sample, which is typically in excess, continually flows past the detection zone resulting in the build-up of captured analyte complex Such devices are simple to use, and the result may be determined visually, without the need for an electronic reader. They are also semi-quantitative, giving rise to either a positive or negative result. Due to the nature of the test, it is necessary to wait for a certain period of time such that a sufficient amount of the labelled analyte complex is captured in the detection zone. If a result were read too early, it might be interpreted as being negative, even though analyte were in fact present in the sample. In view of this, instructions requiring the user to wait for a prescribed period of time after the sample has been applied in order to view the result often accompany the test. Other methods include a signal that is generated after a particular period of time has elapsed which indicates to the user that a sufficient period of time has elapsed in order to read the test, as disclosed in our copending application no PCT/EP03/00274.

EP653625 discloses a lateral flow assay test-strip for use in combination with an assay reader the whereby the extent of binding of particulate label is determined optically (i.e. by assay reader). The reader further incorporates a timing mechanism such that the result is displayed after a preset period, thus removing the need for the user to time the test.

U.S. Pat. No. 5,837,546 discloses an integrated reader and test-strip wherein the test-strip is provided with additional electrodes which sense the presence of fluid on the test-strip which generates a signal to switch on the sensing electronics.

The above tests however, require a preset time to have elapsed before the result is read or displayed. This is not always convenient, for example in the case wherein the test in used in an emergency room procedure and the time to result is vital. For instance, some commercial lateral flow assay-based test kits for markers of cardiac damage require as much as 15 minutes or so for the assay to be completed. In other cases, such as a pregnancy test, there is a natural desire on the part of the user to have the result as soon as possible.

SUMMARY

The present disclosure provides assay devices comprising a reader for use with, or in integral combination with, an assay test strip. The reader can, under certain circumstances, determine a positive or negative result (i.e., the presence and/or amount of an analyte in a test sample) before an assay has completed.

In some embodiments, an assay result reading device may include a computation circuit responsive to a signal representing the amount of an analyte or the rate of accumulation of an analyte. The circuit compares the signal to a first threshold and compares the signal to a second threshold, the second threshold being less than the first threshold. The circuit generates an output signal indicative of a first result and terminates the assay if the signal exceeds the first threshold. The circuit generates an output signal indicative of a second result and terminates the assay if the signal is less than the second threshold.

In some embodiments, a method for determining the outcome of an assay includes performing the assay to generate a signal representing the amount of an analyte or the rate of accumulation of an analyte; comparing the signal with first and second threshold values; and declaring the result of the assay if the determined rate or amount of signal accumulation exceeds the upper threshold value or is below the lower threshold value.

DETAILED DESCRIPTION

Figure 1:
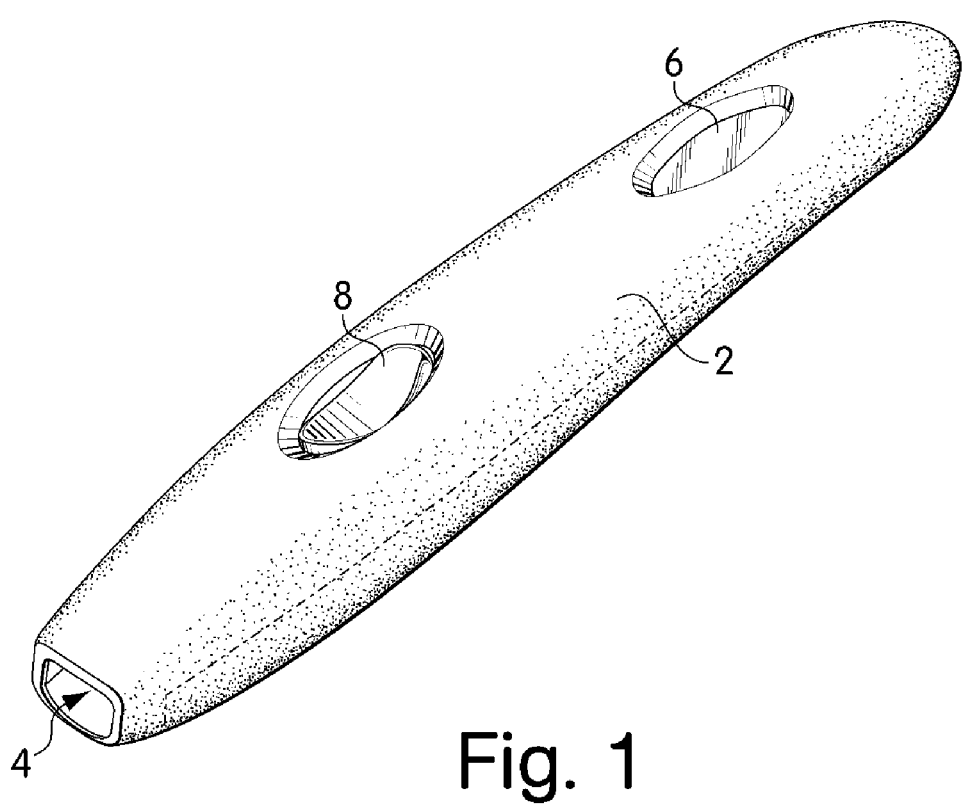
FIG. 1 is a perspective view of one embodiment of an assay result reading device in accordance with the present disclosure.

It is preferred, but by no means essential, that the assay is a lateral flow type assay, in which a liquid sample, possibly comprising the analyte of interest, is applied to a liquid transport means (typically comprising a porous carrier, such as nitrocellulose) and migrates there along. Assays of this type are well known to those skilled in the art and are disclosed, for example, in EP0291194.

The signal which accumulates during performance of the assay may be anything suitable for the purpose. Conveniently the signal accumulation comprises formation or accumulation of a readily detectable substance (e.g. a coloured reaction product). More especially the assay preferably comprises accumulation of a labelled reagent, typically deposition or accumulation of the labelled reagent in the test zone or detection zone of a lateral flow assay stick. The label may be, for instance, an enzyme, a radiolabel, a fluorochrome, a coloured particle or the like. In particular the assay conveniently involves the accumulation of a specific binding reagent in the detection zone of a lateral flow assay stick, the specific binding reagent being labelled with a particle of gold or a coloured polymer, such as latex.

Generally speaking, presence of the analyte of interest in the sample will tend to cause accumulation of signal. However, in other formats (especially for example, competition or displacement formats), it is the absence of the analyte of interest which may cause the accumulation of the relevant signal.

Again, generally speaking, in those embodiments of the device and method of the present disclosure where presence of the analyte of interest leads to accumulation of the signal, the upper threshold value is set such that signal levels below this value are regarded as negative (i.e. the analyte is not present) and levels above are regarded as positive.

If after a certain period of time, the rate or amount of signal accumulation has not reached the lower threshold limit, it is considered that the signal will never reach the upper threshold even if the reaction were allowed to proceed to completion, and an early negative result is then displayed. This would represent the case of a fluid sample having a very low analyte concentration.

Conversely, a result can be promptly displayed if the rate or amount of signal accumulation crosses the upper threshold limit. In the case of a high analyte concentration, the reading will cross the upper threshold limit at an earlier time and therefore an earlier than usual result may be displayed.

In the intermediate case wherein the rate or amount of signal accumulation crosses the lower threshold limit before a certain period of time has elapsed but does not exceed the upper threshold, the reader will wait until the reading crosses the upper threshold before displaying a positive result. If the reading does not pass the upper threshold before a further second period of time has elapsed, a negative result is displayed.

Thus the device is able to display the results as soon as conveniently possible rather than necessarily wait for a preset time to elapse. A device in accordance with the present disclosure can therefore generally indicate an assay result more quickly, especially where the analyte concentration is very high or very low.

The reaction which leads to signal accumulation may be any suitable reaction e.g. a conventional chemical reaction between two chemical entities, or an enzyme-catalysed reaction or reaction requiring some other catalyst, or may be a binding reaction. Preferred binding reactions will involve the binding of at least one biological molecule. More especially, the reaction will preferably involve the binding of members of a specific binding pair ("sbp"). Sbps are well known to those skilled in the art and include, inter alia, enzyme/substrate, antibody/antigen, and ligand/receptor pairs.

A preferred reaction involves the binding of a labelled analyte/reagent complex to specific binding reagent immobilised in a detection zone of a lateral flow assay stick, the signal being accumulation of the label in the detection zone.

The assay result reader will typically comprise an optical detection system to detect accumulation of the label. Conveniently the reader device will comprise means of generating a signal (typically a digital signal) which is proportional to the amount of label accumulated. Desirably the optical detection system may measure an optical property, such as the amount of light reflected and/or transmitted from a detection zone in which the label accumulates. Suitable optical systems are known to those skilled in the art and are disclosed, for example, in EP 0653625.

The preferred optical detection system will comprise at least one light source and at least one photodetector (such as a photodiode). Preferred light sources are light emitting diodes or LED's. Reflected light and/or transmitted light may be measured by the photodetector. For the purposes of this disclosure, reflected light is taken to mean that light from the light source is reflected from the porous carrier or other liquid transport means onto the photodetector. In this situation, the detector is typically provided on the same side of the carrier as the light source. Transmitted light refers to light that passes through the carrier and typically the detector is provided on the opposite side of the carrier to the light source. For the purposes of a reflectance measurement, the carrier may be provided with a backing such as a white reflective MYLAR® plastic layer. Thus light from the light source will fall upon the carrier, some will be reflected from its surface and some will penetrate into the carrier and be reflected at any depth up to and including the depth at which the reflective layer is provided. Thus, a reflectance type of measurement may actually involve transmission of light through at least some of the thickness of the porous carrier.

In a preferred embodiment the assay result reading device comprises a housing formed from a light-impermeable material, conveniently a synthetic plastics material such as polycarbonate, ABS, polystyrene, high density polyethylene, or polypropylene or polystyrol containing a suitable light-blocking pigment.

The housing of the assay result reader typically comprises an aperture such that a test strip may be releasably inserted into and (preferably) engaged with the housing. The housing is designed such that ambient light entering the interior of the reader is kept to an absolute minimum. Desirably suitable alignment and fixing means are provided within the housing such that the test strip remains in a fixed position when inserted. The light sources are arranged in the housing such that, when the test strip has been correctly inserted, they are correctly aligned with the respective zone to be measured.

The assay test strip may be any conventional lateral flow assay test strip such as those disclosed in EP291194 or U.S. Pat. No. 6,352,862. The test strip preferably comprises a porous carrier containing a particulate labelled specific binding reagent and an unlabelled specific binding reagent. The light sources and corresponding photodetectors are preferably so aligned such that during use, light from the light sources falls upon the respective zones on the porous carrier and is reflected or transmitted to the respective photodetectors. The photodetectors generate a current proportional to the amount of light falling upon it which is then fed through a resistor to generate a voltage. The amount of light reaching the photodetector depends upon the amount of coloured particulate label present and therefore the amount of analyte. Thus the amount of analyte present in the sample may be determined. This method of optically determining the analyte concentration is described more fully in EP653625.

In a typical embodiment, the assay result reading device will comprise one or more of the following: a central processing unit (CPU) or microcontroller; one or more LED's; one or more photodetectors; a power source; and associated electrical circuitry. The power source may be a battery or any other suitable power source (e.g. a photovoltaic cell).

Conveniently the CPU or microcontroller will be programmed so as determine, from the output of the photodetectors, the rate or amount of signal accumulation and to compare this with the upper and lower threshold values.

In order to declare the assay result the reader will generally possess some manner of indicating or communicating the result of the assay to a user. This may take the form, for example, of an audible or visible signal. Desirably the device will comprise a visual display to display the assay result. This may simply take the form of one or more LED's or other light sources, such that illumination of a particular light source or combination of light sources conveys the necessary information to the user. Alternatively the device may be provided with an alphanumeric or other display, such as an LCD. In addition, or as an alternative, to displaying the assay result, the device may also display or indicate in some other way to the user whether or not the result of the particular assay should be disregarded e.g. because a control result has failed. If the reading device determines that a particular assay result should be disregarded it may prompt the user to repeat the assay. Displays suitable for displaying this sort of information are known to those skilled in the art and disclosed, for example, in WO 99/51989.

For the avoidance of doubt, it is expressly stated that any of the features described herein as "preferred", "desirable", convenient", "advantageous" or the like may be adopted in an embodiment in combination with any other feature or features so-described, or may be adopted in isolation, unless the context dictates otherwise.

Advantageously the reader device will have some means of determining elapsed time, such as an integral clock device.

Preferably the reading device is activated when an assay device is inserted into the reader device. This may be achieved by the user pressing a switch or button but, more preferably, is effected automatically, such that insertion of an assay device in the correct orientation and into the correct position within the reader causes activation thereof. To facilitate this, it is preferred that the reader and the assay device are shaped and dimensioned so as to provide a precise three dimensional fit. This concept is disclosed and described in EP 0833145. In particular activation of the reader and/or insertion of an assay device into the reader may trigger the reader to commence timing.

Desirably the reader is so programmed as to make a first determination of the rate or amount of signal accumulation after a predetermined time interval. (Say, for example, 10 seconds after activation). If the rate or amount of signal accumulation exceeds the upper threshold or is below the lower threshold, and the control values (if any) are within acceptable limits, the assay can be safely terminated and the results (positive, negative, or a semi-quantitative result) indicated to the user. If however the determined rate or amount of signal accumulation is above the lower threshold but below the upper threshold, the assay must be continued. The signal in this instance may be said to be an intermediate signal.

Typically there is an end-point, $t_e$, at which the reader device considers the assay complete. If the signal is still below the upper threshold value at $t_e$ the result of the assay is negative (in those formats in which it is the presence of the analyte of interest which leads to formation of the signal). The end-point of the assay may not necessarily be at completion of the reaction. Indeed, the end-point $t_e$ will normally be considered to have been reached before the reaction is complete.

The $t_e$ end point may conveniently be determined by the reader by reference to a particular time point (i.e. $t_e$ may be considered to occur a particular amount of time after commencement of the assay e.g. a particular interval after activation of the reader and/or insertion of an assay stick into the reader and/or application of the sample to the test stick). For the purposes of illustration, te will typically occur between 1 and 10 minutes, preferably between 1 and 5 minutes after commencement of the assay.

Desirably the assay result reader will be programmed so as to repeat the test measurement if an intermediate signal is obtained. In a simple embodiment the measurement is repeated at $t_e$. Preferably however the measurement is repeated one or more times before the end point. Most preferably the reader device is programmed to repeat the measurement at regular intervals (say, for instance 1 second or 5 second intervals) until the signal exceeds the upper threshold or until $t_e$, which ever occurs first.

Inclusion of a clock or other timing device in the assay result reader is desirable so that the reader can automatically take measurements at predetermined time points without further user input.

Thus, for example, the reader may be programmed to take measurements at an initial time point $t_0$ and, if necessary to make repeated measurements at any desired interval thereafter until the signal exceeds the upper threshold or $t_e$ is reached, as described above.

In addition, a clock or other timing device facilitates the reading device in determining the rate of signal accumulation. If measurements of the amount of signal are taken at two or more time points (with a known temporal separation), then the rate of signal accumulation may readily be calculated.

It should be noted that the rate or amount of signal accumulation could be measured either in absolute terms or as a relative valve (e.g. compared to a control or other comparison value, optionally obtained from a substantially contemporaneous reaction).

EXAMPLES

Example 1

An embodiment of an assay result reading device is shown in FIG. 1.

The reading device is about 12 cm long and about 2 cm wide and is generally finger or cigar-shaped. In preferred embodiments, the housing is no larger than about 12 cm long, about 2.5 cm wide, and about 2.2 cm tall. However, any convenient shape may be employed, such as a credit card shaped reader. The device comprises a housing 2 formed from a light-impermeable synthetic plastics material (e.g. polycarbonate, ABS, polystyrene, high density polyethylene, or polypropylene or polystyrol containing an appropriate light-blocking pigment, such as carbon). At one end of the reading device is a narrow slot or aperture 4 by which a test strip (not shown) can be inserted into the reader.

On its upper face the reader comprises two oval-shaped apertures. One aperture accommodates the screen of a liquid crystal display 6 which displays information to a user e.g. the results of an assay, in qualitative or quantitative terms. The other aperture accommodates an eject mechanism 8 which, when actuated, forcibly ejects an inserted assay device from the assay result reading device.

The assay device for use with the reading device is a generally conventional lateral flow test stick e.g. of the sort disclosed in U.S. Pat. No. 6,156,271, U.S. Pat. No. 5,504,013, EP 728309 or EP 782707. The assay device and a surface or surfaces of the slot in the reader, into which the assay device is inserted, are so shaped and dimensioned that (1) the assay device can only be successfully inserted into the reader in the appropriate orientation; and (2) there is a precise three dimensional alignment of the reader and an inserted assay device, which ensures that the assay result can be read correctly the reader.

A suitable assay device/reader device combination exhibiting this precise three dimensional alignment is disclosed in EP 833145.

When an assay device is correctly inserted into the reader, a switch is closed which activates the reader from a "dormant" mode, which is the normal state adopted by the reader, thereby reducing energy consumption.

Figure 2:
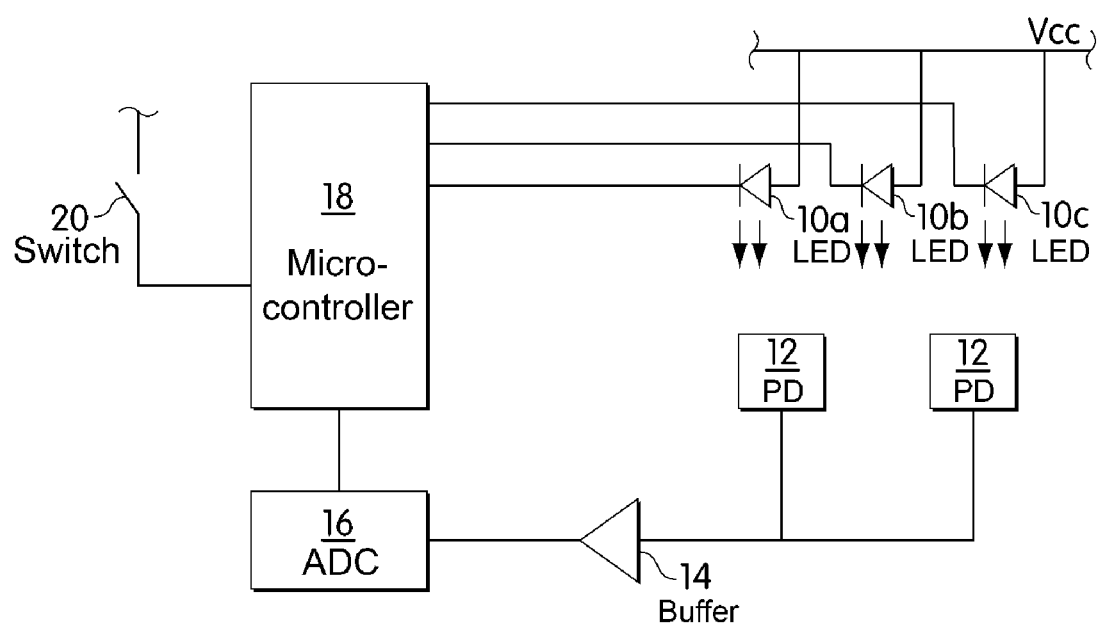
FIG. 2 is a schematic representation of some of the components of the embodiment illustrated in FIG. 1.

Enclosed within the housing of the reader (and therefore not visible in FIG. 1) are a number of further components, illustrated schematically in FIG. 2.

Referring to FIG. 2, the reader comprises three LED's 10$a,b$, and $c$. When a test stick is inserted into the reader, each LED 10 is aligned with a respective zone of the test stick. LED 10$a$ is aligned with the test zone, LED 10$b$ is aligned with the reference zone and LED 10$c$ is aligned with the control zone. Respective photodiodes 12 detect light reflected from the various zones and generate a current, the magnitude of which is proportional to the amount of light incident upon the photodiodes 12. The current is converted into a voltage, buffered by buffer 14 and fed into an analogue to digital converter (ADC, 16). The resulting digital signal is read by microcontroller 18.

In a simple arrangement, a separate photodiode is provided to detect from each zone (i.e. the number of photodiodes equals the number of zones from which reflected light measurements are made). The arrangement illustrated in FIG. 2 is more sophisticated, and preferred. Two photodiodes 12 are provided. One photodiode detects light reflected from the test zone and some of the light reflected from the reference zone. The other photodiode 12 detects some of the light reflected from the reference zone and the light reflected from the control zone. The microcontroller 18 switches on the LED's 10 one at a time, so that only one of the three zones is illuminated at any given time—in this way the signals generated by light reflected from the respective zones can be discriminated on a temporal basis.

FIG. 2 further shows, schematically, the switch 20 which is closed by insertion of an assay device into the reader, and which activates the microcontroller 18. Although not shown in FIG. 2, the device further comprises a power source (typically one or two button cells), and an LCD device responsive to output from the microcontroller 18.

In use, a dry test stick (i.e. prior to contacting the sample) is inserted into the reader, this closes the switch 20 activating the reader device, which then performs an initial calibration. The intensity of light output from different LED's is rarely identical. Similarly, the respective photodetectors are unlikely to have identical sensitivities. Since such variation could affect the assay reading an initial calibration is effected, in which the microcontroller adjusts the length of time that each of the three LED's is illuminated, so that the measured signal from each of the three zones (test, reference and control) is approximately equal and at a suitable operating position in a linear region of the response profile of the system (such that a change in intensity of light reflected from the various zones produces a directly proportional change in signal).

After performing the initial calibration, the device performs a further, finer calibration. This involves taking a measurement ("calibration value") of reflected light intensity for each zone whilst the test stick is dry—subsequent measurements ("test values") are normalised by reference to the calibration value for the respective zones (i.e. normalised value=test value/calibration value).

To conduct an assay, a sample receiving portion of the test stick is contacted with the liquid sample. In this case of a urine sample, the sample receiving portion may be held in a urine stream, or a urine sample collected in a receptacle and the sample receiving portion briefly (for about 5-10 seconds) immersed in the sample. Sampling may be performed whilst the test stick is inserted in the reader or, less preferably, the stick can be briefly removed from the reader for sampling and then reintroduced into the reader.

Measurements of reflected light intensity from one or more (preferably all three) of the zones are then commenced, typically after a specific timed interval following insertion of the test stick into the reader. Desirably the measurements are taken at regular intervals (e.g. at between 1-10 second intervals, preferably at between 1-5 second intervals). The measurements are made as a sequence of many readings over short (10 milliseconds or less) periods of time, interleaved zone by zone, thereby minimising any effects due to variation of ambient light intensity which may penetrate into the interior of the reader housing.

Example 2

Figure 3:
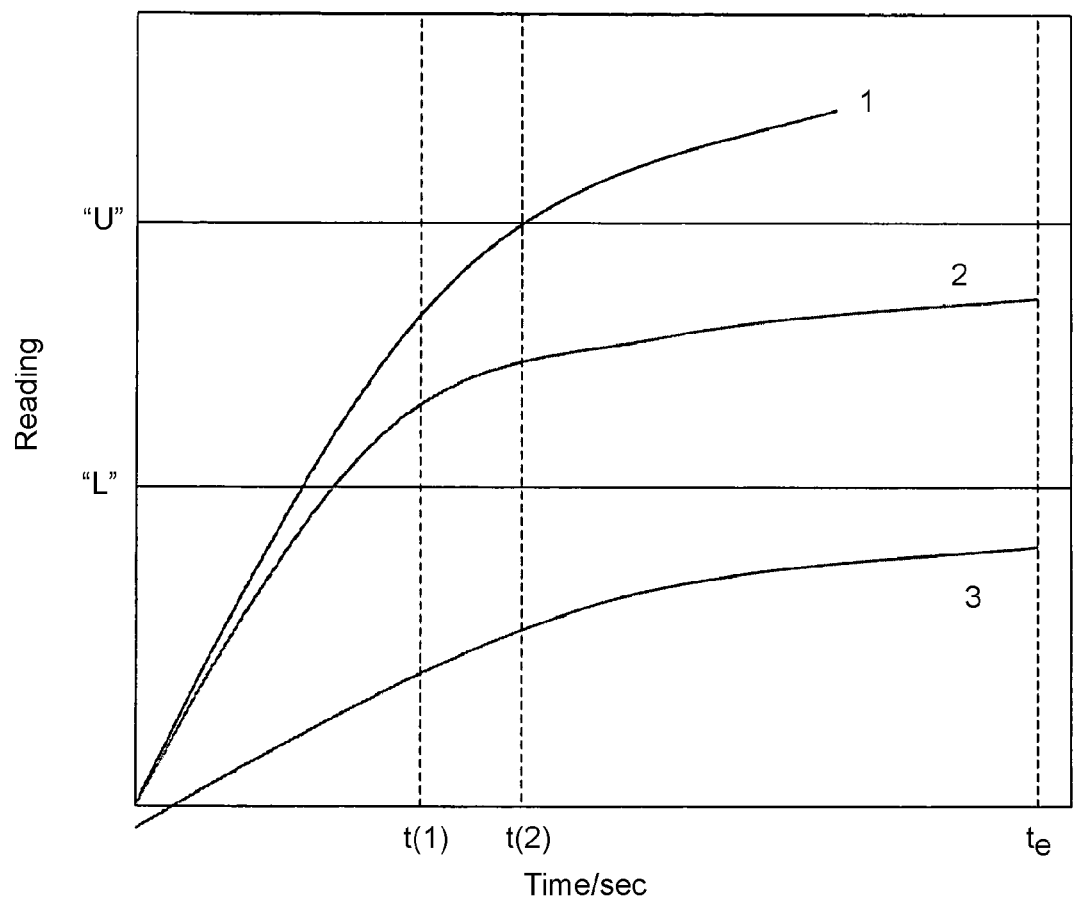
FIG. 3 is a graph of typical results for reading (i.e. signal) against time.

FIG. 3 shows typical results for three different samples, in terms of amount of signal ("Reading", in arbitrary units) against time (in seconds).

The amount of signal is a measure of the light absorbed, or the decrease in light reflected, from the test zone of a lateral flow test stick as might be determined using the assay result reader described in the preceding example. In the presence of the analyte of interest, a coloured particulate labelled binding reagent accumulates in the test zone. The coloured particulate label absorbs some of the light incident upon the test zone, and this reduces the amount of light reflected therefrom which is available for detection by a suitably positioned photodetector. The higher the concentration of analyte, the more rapid the rate of accumulation of label in the test zone and the stronger the "signal".

Plot 1 illustrates a typical graph which might be obtained for a liquid sample which contains a high concentration of analyte. Plot 3 illustrates a typical graph which might be obtained for a liquid sample which contains a very low concentration of analyte. Plot 2 illustrates a typical graph which might be obtained for a liquid sample which contains an intermediate concentration of analyte.

Also shown on the graph are two horizontal lines which indicate the upper threshold ("U") and lower threshold ("L") values respectively.

Referring to plot 1, the reader is programmed to make an initial reading at t(1), a certain predetermined length of time after commencement of the assay. The reading obtained is below the value of "U", so an early positive result cannot be declared at t(1).

Equally, the reading is above the value of "L", so an early negative result cannot be declared at t(1) either. In this situation, the reader is programmed to repeat the measurement after a further, predetermined period of time has elapsed, at t(2). At t(2) the reading for plot 1 has just exceeded the value of U, so the reader can promptly indicate that the result is positive, via the LCD device.

Referring to plot 3, at t(1) the initial reading is below the value of L, so the reader can promptly declare a negative result, since it can be predicted that the value will never exceed the upper threshold before the predetermined endpoint of the assay $t_e$.

Referring to plot 2, the initial reading at time t(1) is, similar to that for plot 1, below the value of U but above the value of L, so an early positive or negative result cannot be declared. The same is true at t(2). If desired, the reader can be programmed to make any number of further readings at t(3), t(4) etc. until the final reading is taken at $t_e$. For plot 2, the final reading at $t_e$ is still below the value of U, so the assay result would be negative.

The following comments apply generally, not just to the example described immediately above. It should be noted that, rather than measure absolute readings, values may be calculated with respect to the rate of change of reading with respect to time, or d(reading)/d(time). Alternatively, the rate of change of slope with respect to time may be measured or $d^2(reading/d)time)^2$ or the integral $\int d(reading)$ with respect to two or more time values, namely the area defined by the curve. This has the advantage that reading is averaged over time, which smooths any anomalies. Alternatively, the rate of change of slope with respect to time may be measured or $d^2(reading/d)time)^2$. As a further alternative, all or some of the above measurements may be made in combination to yield a result. Thus rather than provide an early result based upon the value of the reading exceeding a lower or upper threshold, the reader may make this evaluation based upon calculation of a first or second differential, an integral or combination of one or more thereof. Furthermore, an early result may be promptly declared after the reading has exceeded the lower threshold but the reader determines that the result will not exceed the upper threshold value before the reading has reached equilibrium Furthermore it may be noted that the values of the at least upper and lower threshold limits may be adjusted during the course of the assay reading. This may occur on the basis of the readings obtained earlier in the course of the assay. It is preferable however that these values remain constant during the course of an individual assay.

As an alternative to promptly declaring the result, the reader may wait for a certain defined period before declaring a result. This provides an extra control feature, such that for example a result is not declared before various control checks have been made on either the assay strip, the reader or both. Such a situation might occur for a sample having an exceedingly high or low analyte concentration.

Example 3

An assay result reading device was created for making pregnancy determinations based on the concentration of hCG in urine. The test strip includes anti-hCG antibody coupled to a chromophore.

The upper threshold was set at 10% attenuation gain (AG) (signal vs reference), and the lower threshold was set at 6% attenuation gain (control vs ref). 10% AG corresponds to approximately 15 mIU hCG for a new test-strip and 25 mIU for an aged test-strip (aging is believed to cause decay of the antibody, resulting in an apparent increase of signal) and 6% AG corresponds to approx. 5 mIU. In other embodiments, the upper threshold can be set between about 10 and about 90% AG, and the lower threshold between about 1% and about 9%, although in principle other value ranges could be chosen.

The initial time reference (t=0) is set when the control vs reference signal passes through zero. This means that the sample fluid has reached the control line. The timer is then started. The analyte signal is compared to the threshold values as described previously. The earliest time point for a positive (pregnant) result is set at 20 seconds, and the earliest point for a negative result is set at 60 seconds. In other embodiments, of course, other time periods may be set.

The disclosed devices and methods may, naturally, be adapted for use with a wide variety of analytes. In particular, it should be noted that the disclosed devices and methods may be used in situations in which a negative result is expected only in the absence of analyte, and also in situations where a negative result is appropriate even when the analyte is present in some amount. An example of the first situation is a test for a pathogen, such as HIV or strep A. However, even in the absence of analyte, a lower threshold is still set and threshold test employed, because non-specific binding may otherwise result in a false-positive background reading.

An example of the second situation is an assay result reader for ovulation that measures luteinizing hormone (LH), because LH is normally present at a basal level and surges shortly before ovulation; a positive result is desired during the surge, and a negative result during the basal level.

Example 4

The above-described examples refer to assay result reading devices that work as one-time tests; i.e., a single test strip is assayed for a single test result. The threshold values typically remain fixed from test to test for reliability and reproducibility.

However, some embodiments may employ a series of test strips in order to track the amount of an analyte over time, and to adjust the threshold values from strip to strip in the series order to provide precise results.

One example of such a system is an assay result reader that measures luteinizing hormone (LH) over several days to predict ovulation based on detecting the "LH surge" shortly before ovulation. In a typical procedure, a first measurement is made. If it is above a certain upper threshold (for example, greater than 16% AG), a positive result indicating "LH surge" is returned. If the measurement is below this threshold, then the upper threshold for the next test is adjusted, depending on the level measured. For example, if the signal is lower than 7% AG, the upper threshold is lowered to 13%. If the measurement for the first test-strip is lower than respectively 5% or 3%, values of respectively 12% and 11% are chosen.

Thus, the algorithm chooses the threshold on the basis of the previous day's measurement, but it could also be an average of the previous days measurements. Thus in general, the thresholds need not neccessarily be fixed.

Example 5

In some embodiments, the assay result reading device includes a memory system that stores prior test results accumulated over a period of time. For example, the device may be configured for testing for the presence of a drug of abuse or a metabolite thereof, and the memory system can store periodic test results. The device also includes a system for viewing or retrieving test results, such as by a display, and electronic connection, or the like.

Example 6

In some embodiments, the assay result reading device includes a memory system that stores test profiles for a variety of analytes. A profile can include, for example, the upper threshold and the lower threshold. The profile can further include time periods for performing threshold comparisons. In this manner, a single assay result reading device may be used to perform a variety of analyte assays.

The device further includes a selection system that selects the appropriate profile for the desired analyte. In some embodiments, the selection system can be a switch that a user sets to the desired test. In other embodiments, the selection system detects a feature on an assay test strip indicative of the analyte to be measured. For example, the test strip may have a bar code or other optical pattern. Alternatively, a test strip may be configured so that it remits light of a certain frequency or in a frequency range that is characteristic for a particular analyte. The memory system has a look-up table that the selection system may access to identify an analyte based on the remitted light frequency.

Example 7

An assay result reader according to the present disclosure may also include a system for detecting flow rate of a fluid sample, such as one described in U.S. patent application Ser. No. 10/742,459, Dec. 19, 2003.

Example 8

An assay result reader according to the present disclosure may also include an optical arrangement such as those described in U.S. patent application Ser. No. 60/508,001, filed Oct. 2, 2003.

Figure 4:
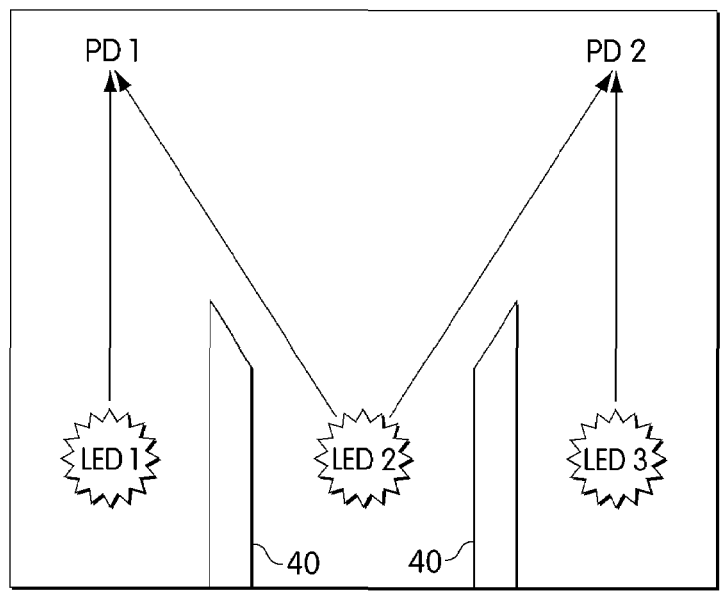
FIGS. 4-6 are schematic representations of an embodiment incorporating a preferred light source/photodetector arrangement.
Figure 5:
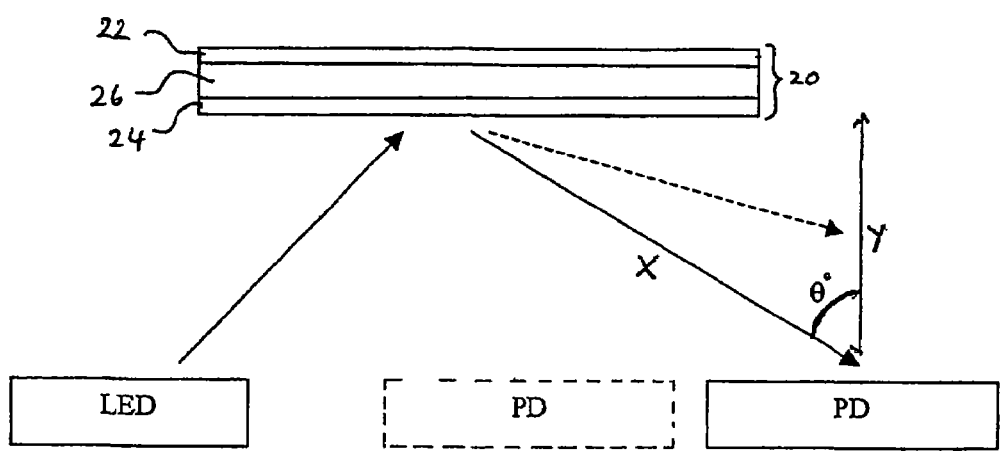
Figure 6:
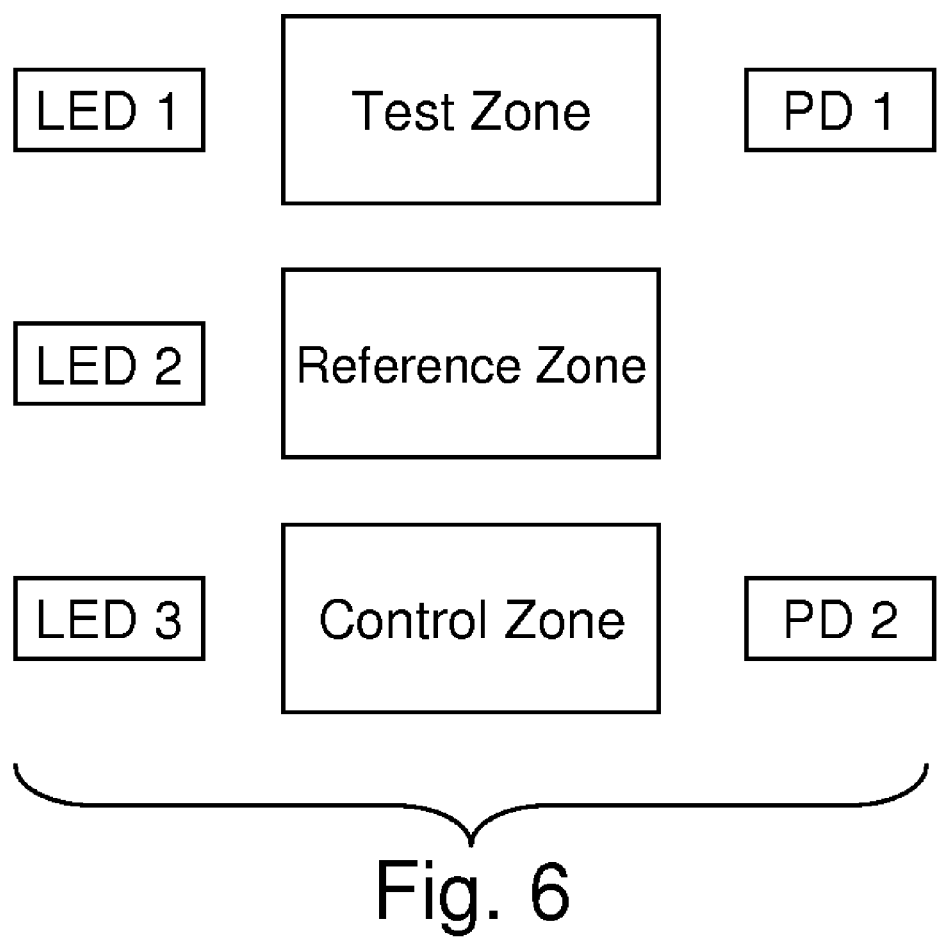

FIG. 4 is a schematic representation of the layout of the 3 LED/2 Photodiode optical system described in Example 1. FIG. 5 is a schematic representation of a side elevation of one LED/Photodiode, and illustrating their position relative to a nitrocellulose test strip. FIG. 6 is a schematic plan view of the LED/Photodiode arrangement, again illustrating their position relative to a test strip.

Referring to FIG. 4, an optics block component for accommodation within an assay result reading device may include three LEDs (LED 1, 2 and 3) and two photodetectors (PD1 and PD2). Light from LED 1 illuminates a test zone of a test strip (not shown) inserted into the reader. Light reflected from the test zone is detected by PD1. Light from LED 3 illuminates a control zone of the test strip and light reflected therefrom is detected by PD2. Light from LED 2 illuminates a reference zone of the test strip.

Each LED is optically isolated by light-impermeable baffles 40, which ensure that the various LEDs are capable of illuminating only its respective zone of the test strip. However the surfaces of the baffles facing LED2 are angled so as to allow LED2 to illuminate a slightly wider portion of the test strip than LED1 or 3, and this in turn allows light reflected from the reference zone to be detected by both PD1 and PD2.

The relative positioning of the test strip, LEDs and photodiodes may be better understood by reference to FIGS. 5 and 6.

Referring to FIG. 5, a test strip 20 is inserted into the reading device above the plane of the LEDs and photodiodes. The test strip 20 is of laminate construction including an uppermost backing layer 22 of reflective opaque white MYLAR®, a synthetic plastics material, and a lowermost front layer 24 of clear MYLAR®. Sandwiched between the MYLAR® layers 22, 24 is a layer of porous material 26 (typically nitrocellulose). The purpose of the MYLAR® layers is to protect the delicate nitrocellulose and provide mechanical strength and rigidity. In addition, the opaque backing layer 22 is relatively highly reflective, and this serves to improve contrast: relatively little light is absorbed by the layers 24, 26 and much of the light incident upon the various zones would therefore tend to pass straight through the test strip, but the reflective MYLAR® backing layer 22 ensures that this light is reflected. In addition, since the particulate label accumulating in the nitrocellulose layer 26 absorbs only a portion of the light as it passes through in a generally upwards direction, the label has in effect a second chance to absorb light as it passes back through the test strip 20 in a generally downwards direction, having been reflected by the opaque MYLAR® backing layer 22. This significantly improves the signal-to-noise ratio.

As can be seen from FIGS. 5 and 6, the photodiodes PD1 and PD2 are aligned with their respective LEDs, LED1 and 3, but are offset, in that the LEDs lie towards one side of the test strip while the photodiodes lie towards the other side. Having the photodiodes offset in this way avoids, or at least reduces, the amount of specular reflection from the clear MYLAR® layer 24 detected by the photodiodes (i.e. light which is reflected directly from the initial MYLAR® layer 24 without ever penetrating into the nitrocellulose layer—detection of such reflections would decrease the signal:noise ratio).

Referring to FIG. 5 the relationship between signal intensity (I) and the angle (θ) of the reflected light relative to the photodiode is $I \propto \cos \theta^4$. Furthermore, the relationship between signal intensity (I) and the distance (x) of the photodiode from the reflecting object is $I \propto 1/x^2$ (i.e. the inverse square law). It is apparent that, in view of the inverse square law, it would generally be preferred to position the photodiodes as close as possible to the test strip (i.e. decrease x), so as to increase the signal intensity I. However, merely decreasing the vertical separation y between the photodiode and the test strip would increase angle θ, decreasing the value of cos θ and therefore tend to reduce the signal intensity.

An alternative approach to improve signal intensity would be to re-position the photodiode nearer the center of the system (indicated by the dotted lines in FIG. 5) which would simultaneously decrease x and θ. However, this is found to be undesirable as it increases the likelihood of detecting specular reflections. Accordingly an aligned but offset position for the photodiodes provides an optimal compromise of the considerations.

It may be noted from FIG. 6 that photodiode 1 is aligned with the test zone and photodiode 2 is aligned with the control zone. This alignment ensures that any variation of the relative positioning of the test strip and assay reader has minimal effect on the angle θ. While PD1 and PD2 are not aligned with the reference zone, and are therefore subject to a relatively large (and therefore undesirable) angle of θ, this problem is not significant because (i) the use of two detectors to read the reference zone allows for compensation of any positional variation, since relative movement of the test strip so as to increase θ for one photodetector may decrease θ for the other photodetector; and (ii) the reference zone is used to give a background reading for calibration purposes—the photodiodes are not required to measure the signal intensity from a narrow line (as with the test or control zones), and so the measurement of the reference zone signal is inherently less sensitive to variation from mis-positioning.

All patents and patent applications referred to in this disclosure are hereby incorporated herein in their entireties by this reference.

The invention claimed is:

1. A device for determining the result of an assay, comprising:
   a computation circuit, responsive to a signal representing the amount of an analyte or the rate of accumulation of an analyte, to:
      compare the signal to a first threshold;
      compare the signal to a second threshold, the second threshold being less than the first threshold;
      generate an output signal if the signal exceeds the first threshold or the signal is less than the second threshold, the output signal indicative of a first result if the signal exceeds the first threshold, or, alternatively, the output signal indicative of a second result if the signal is less than the second threshold; and
      terminate the assay if the signal exceeds the first threshold or the signal is less than the second threshold.

2. A device according to claim 1, wherein the first result is a positive result, and the second result is a negative result.

3. A device according to claim 1, wherein the computation circuit is further responsive to the signal to repeat the comparisons and the conditional generation if the signal is between the first threshold and the second threshold.

4. A device according to claim 1, further comprising an optical detection system for measuring the signal.

5. A device according to claim 4, wherein the optical detection system comprises at least one light source and at least one photodetector.

6. A device according to claim 4, wherein the optical detection system comprises at least three light sources and two photodetectors.

7. A device according to claim 6, wherein the at least three light sources comprise three light emitting diodes, and the at least two photodetectors comprise two photodiodes.

8. A device according to claim 1, further comprising a timer coupled to the computation circuit.

9. A device according to claim 8, wherein the comparisons are performed within about one second of each other.

10. A device according to claim 8, wherein the comparisons are performed within about 60 seconds of each other.

11. A device according to claim 8, wherein the comparisons are performed at least about 30 seconds apart.

12. A device according to claim 1, further comprising a housing enclosing the computation circuit.

13. A device according to claim 12, wherein the housing is no larger than about 12 cm long, about 2.5 cm wide, and about 2.2 cm tall.

14. A device according to claim 12, further comprising at least one light source and at least one photodetector, and wherein:
   the housing defines an aperture for receiving at least a portion of a test strip inside the device, the assay strip having at least one zone, and
   the aperture, the light source, and the photodetector are positioned, sized and shaped so that, upon insertion of the test strip, light emitted from the light source is incident on the zone, and light emanating from the zone is incident on the photodetector, and wherein the photodetector generates a signal representing an amount of an analyte in the zone.

15. A device according to claim 14, wherein the housing is no larger than about 12 cm long, about 2.5 cm wide, and about 2.2 cm tall.

16. A device according to claim 14, wherein the at least one light source comprises three light sources, and the at least one photodetector comprises two photodetectors.

17. A device according to claim 16, wherein the at least three light sources comprise three light emitting diodes, and the at least two photodetectors comprise two photodiodes.

18. A device accordingly to claim 1, further comprising at least one light source, at least one photodetector, and a test strip having at least one zone, wherein the light source, the photodetector, and the test strip are positioned, sized and shaped so that light emitted from the light source is incident on the zone, and light emanating from the zone is incident on the photodetector, and wherein the photodetector generates a signal representing an amount of an analyte in the zone.

19. A device according to claim 18, wherein the at least three light sources comprise three light emitting diodes, and the at least two photodetectors comprise two photodiodes.

20. A device according to claim 1, further comprising a memory system for storing assay results.

21. A device according to claim 1, wherein the computation circuit is further responsive to the signal to adjust one or both threshold values.

22. An assay result reading device for reading the result of an assay to detect the presence and/or amount of an analyte of interest and wherein the presence or absence, as appropriate, of the analyte of interest causes a reaction which leads to the accumulation of a signal in a time-dependent manner, the device comprising:
   means for determining the rate or amount of signal accumulation;
   means for comparing the determined rate or amount of signal accumulation with an upper threshold value;
   means for comparing the determined rate or amount of signal accumulation with a lower threshold value; and
   means for declaring the result of the assay if the determined rate or amount of signal accumulation exceeds the upper threshold value or is below the lower threshold value or at such time when it is determined that the rate or amount of signal accumulation will not exceed or is not likely to exceed the lower threshold value before the assay has been completed.

23. A method for determining a result of an assay, comprising:
   performing the assay to generate a signal representing the amount of an analyte or the rate of accumulation of an analyte;
   comparing the signal with a first threshold value before the assay reaches equilibrium;
   comparing the signal with a second threshold value before the assay reaches equilibrium; and
   declaring the result of the assay if the determined rate or amount of signal accumulation exceeds the first threshold value or is below the second threshold value.

24. A method of declaring the result or outcome of an assay to detect the presence and/or amount of an analyte of interest, the method comprising:
  performing the assay so as to cause the reaction which leads to the accumulation of a signal in a time-dependent manner;
  determining, before the reaction has reached equilibrium, the rate or amount of signal accumulation;
  comparing the determined rate or amount with an upper and a lower threshold value; and
  declaring the result or outcome of the assay if the determined rate or amount of signal accumulation exceeds the upper threshold value or is below the lower threshold value or at such time when it is determined that the rate or amount of signal accumulation will not exceed or is not likely to exceed the lower threshold value before the assay has been completed.

25. A method according to claim 24, further comprising the step of defining at least an upper and lower threshold value.

26. A device for determining an assay result, comprising:
  a computation circuit, responsive to a signal representing the amount of an analyte or the rate of accumulation of an analyte before the assay reaches equilibrium, to:
    compare the signal to a first threshold;
    compare the signal to a second threshold, the second threshold being less than the first threshold; and
    generate an output signal if the signal exceeds the first threshold or the signal is less than the second threshold, the output signal indicative of a first result if the signal exceeds the first threshold, or, alternatively, the output signal indicative of a second result if the signal is less than the second threshold.

27. A method comprising:
  performing an assay;
  before the assay has reached equilibrium, generating a signal representing the amount of an analyte or the rate of accumulation of an analyte;
  comparing the signal with a first threshold value;
  comparing the signal with a second threshold value; and
  declaring a result of the assay if the determined rate or amount of signal accumulation exceeds the first threshold value or is below the second threshold value.

* * * * *